United States Patent
Rowe

(10) Patent No.: US 10,641,757 B2
(45) Date of Patent: May 5, 2020

(54) SURFACE GAS CORRECTION BY GROUP CONTRIBUTION EQUILIBRIUM MODEL

(71) Applicant: Halliburton Energy Services, Inc., Houston, TX (US)

(72) Inventor: Mathew Dennis Rowe, Lafayette, LA (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 1252 days.

(21) Appl. No.: 14/769,653

(22) PCT Filed: Mar. 26, 2014

(86) PCT No.: PCT/US2014/031888
§ 371 (c)(1),
(2) Date: Aug. 21, 2015

(87) PCT Pub. No.: WO2014/160793
PCT Pub. Date: Oct. 2, 2014

(65) Prior Publication Data
US 2016/0003793 A1  Jan. 7, 2016

Related U.S. Application Data

(60) Provisional application No. 61/805,828, filed on Mar. 27, 2013.

(51) Int. Cl.
*G01N 33/24* (2006.01)
*E21B 49/00* (2006.01)
(Continued)

(52) U.S. Cl.
CPC ......... *G01N 33/241* (2013.01); *E21B 49/005* (2013.01); *E21B 49/08* (2013.01); *G01N 33/2823* (2013.01)

(58) Field of Classification Search
CPC ....... E21B 49/08; E21B 49/005; B01D 53/14; G01N 7/00; G01N 33/241; G01N 33/2823
See application file for complete search history.

(56) References Cited

U.S. PATENT DOCUMENTS 5,663,492 A * 9/1997 Alapati ............... G01N 7/00
203/2
5,889,202 A   3/1999 Alapati et al.
(Continued)

FOREIGN PATENT DOCUMENTS

CN   1415070 A    4/2003
CN   101566061 A  10/2009

OTHER PUBLICATIONS

Liège, Xavier C., "Dissolution of Light Hydrocarbons in Drilling Muds, Prediction of the Nature of Reservoir Fluids Based on Gas Shows," Ph.D. Thesis, Technical University of Denmark, Copenhagen, Denmark, May 1, 2006.
(Continued)

*Primary Examiner* — Regis J Betsch
*Assistant Examiner* — Kaleria Knox

(57) ABSTRACT

Methods and systems are disclosed to determine total hydrocarbons from fluid-carrying fluids and solids from a geological formation during downhole operations. Gas extraction at a well site occurs through a gas extractor at a set pressure, detected temperature, detected density, and controlled volume rate. The quantities of various components of interest are determined from samples of fluid influent and effluent from the wellbore by solving a system of equations of state using a group contribution equilibrium model. Knowing approximate chemical compositions of the liquid fluid and solid phases before contamination with formation materials, with the detection of the gas phase and description of the solid phase from the geological formation, allows for
(Continued)

determination of total detectable hydrocarbons from geological formations at the surface, and their concentrations to be expressed as mole or mass fraction for materials coming from a wellbore while downhole operations.

20 Claims, 3 Drawing Sheets

(51) Int. Cl.
  *E21B 49/08* (2006.01)
  *G01N 33/28* (2006.01)

(56) References Cited

U.S. PATENT DOCUMENTS

| | | | |
|---|---|---|---|
| 6,322,756 B1* | 11/2001 | Arno | B01D 53/14 422/171 |
| 7,392,138 B2 | 6/2008 | Frechin et al. | |
| 8,011,238 B2 | 9/2011 | Hanson | |
| 2006/0076132 A1* | 4/2006 | Nold, III | E21B 49/10 166/264 |
| 2007/0119244 A1* | 5/2007 | Goodwin | E21B 47/10 73/152.28 |
| 2009/0049889 A1 | 2/2009 | Pop et al. | |
| 2010/0294491 A1* | 11/2010 | Zazovsky | E21B 49/087 166/250.01 |
| 2011/0088949 A1* | 4/2011 | Zuo | E21B 49/08 175/48 |
| 2012/0004892 A1 | 1/2012 | Pita et al. | |
| 2014/0260586 A1* | 9/2014 | Van Hal | E21B 49/082 73/152.07 |

OTHER PUBLICATIONS

Office Action issued for Chinese Application No. 201480010099.1, dated Aug. 28, 2017 (12 pages with translation).

Privat et al., "PPR78, A Thermodynamic Model for the Prediction of Petroleum Fluid-Phase Behaviour." XXXVll JEEP 37th Conference on Phase Equilibria, EDP Sciences, Oct. 5, 2011.

International Search Report and the Written Opinion of the International Searching Authority, or the Declaration, dated Nov. 6, 2014, PCT/US2014/031888, 11 pages, ISA/US.

* cited by examiner

US 10,641,757 B2

SURFACE GAS CORRECTION BY GROUP CONTRIBUTION EQUILIBRIUM MODEL

PRIORITY

The present application is a U.S. National Stage patent application of International Application No. PCT/US2014/031888, filed on Mar. 26, 2014, which claims priority to U.S. Provisional Patent Application No. 61/805,828, entitled, "SURFACE GAS CORRECTION BY GROUP CONTRIBUTION EQUILIBRIUM MODEL," filed Mar. 27, 2013, also naming Mathew Dennis Rowe as inventor, the disclosures of which are hereby incorporated by reference in their entirety.

FIELD OF THE DISCLOSURE

The present disclosure relates generally to mud logging or gas logging while drilling and, more specifically, to a method and system for real-time characterization of formation fluids.

BACKGROUND

During drilling operations, formation fluids and gases may become entrapped in drilling fluid. These gases may be extracted at the surface in a mechanical agitation gas trap and analyzed using a gas chromatographer, mass spectrometer, or like equipment to thereby determine a hydrocarbon profile of the formation per lineal foot drilled for the entire depth of the well. In particular, the molar concentrations of the vapor-phase various components of interest are measured by the gas chromatographer, mass spectrometer, or other analytical equipment, and equation of state calculations using this data are then utilized to extrapolate this measured data into a hydrocarbon profile.

Many different equations of state have been developed to describe the thermodynamic and chemical state of a system. The oil and gas industry traditionally uses the Peng-Robinson equation of state for mud logging purposes with moderate success. However, current mud logging techniques suffer from inaccuracies that require correction factors to be determined and applied. For instance, it is a known practice to initially circulate drilling fluid in a bucket while mud logging measurements and correlate the measurements with laboratory testing to determine correction factors prior to drilling. These methods are not practiced in real time due to the need to obtain periodic experimental laboratory testing to obtain accurate results.

DESCRIPTION OF ILLUSTRATIVE EMBODIMENTS

Illustrative embodiments and related methods of the present disclosure are described below as they might be employed in a system or method to determine formation fluid characteristics in real-time. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, illustrative embodiments of the present disclosure provide alternative methods to correct surface fluid data based upon group contribution equations of state and/or phase equilibrium during real-time downhole operations. As a result, the amount of total hydrocarbons in multiphase downhole fluid (i.e., carrying fluids and solids) recovered from a geological formation are determined in real-time. In one illustrative generalized method, gas extraction at the well site occurs through a gas extractor at a set pressure, detected temperature, detected density, and controlled volume rate. The quantities of various species/components of interest are determined from samples of drilling fluid into (i.e., influent) and out of (i.e., effluent) the wellbore, via the gas extractor, by solving a system of equations of state using a group contribution equilibrium model. Knowing an approximate chemical composition of the liquid fluid phase and solid phase before contamination with geological formation materials, in conjunction with the detection of the gas phase and description of the solid phase from the geological formation, allows for determination of total detectable hydrocarbons extracted from the formation. Moreover, as will be described in more detail below, the difference in compositions of fluid influent and effluent of the well bore may be used to determine the material generated by/absorbed from the geological formation, thus maintaining the integrity of subsequent fluid analysis.

Although the following description focuses on drilling applications, illustrative embodiments of the present disclosure may be utilized in any downhole operation in which fluid flows into or out of the wellbore.

Figure 1:
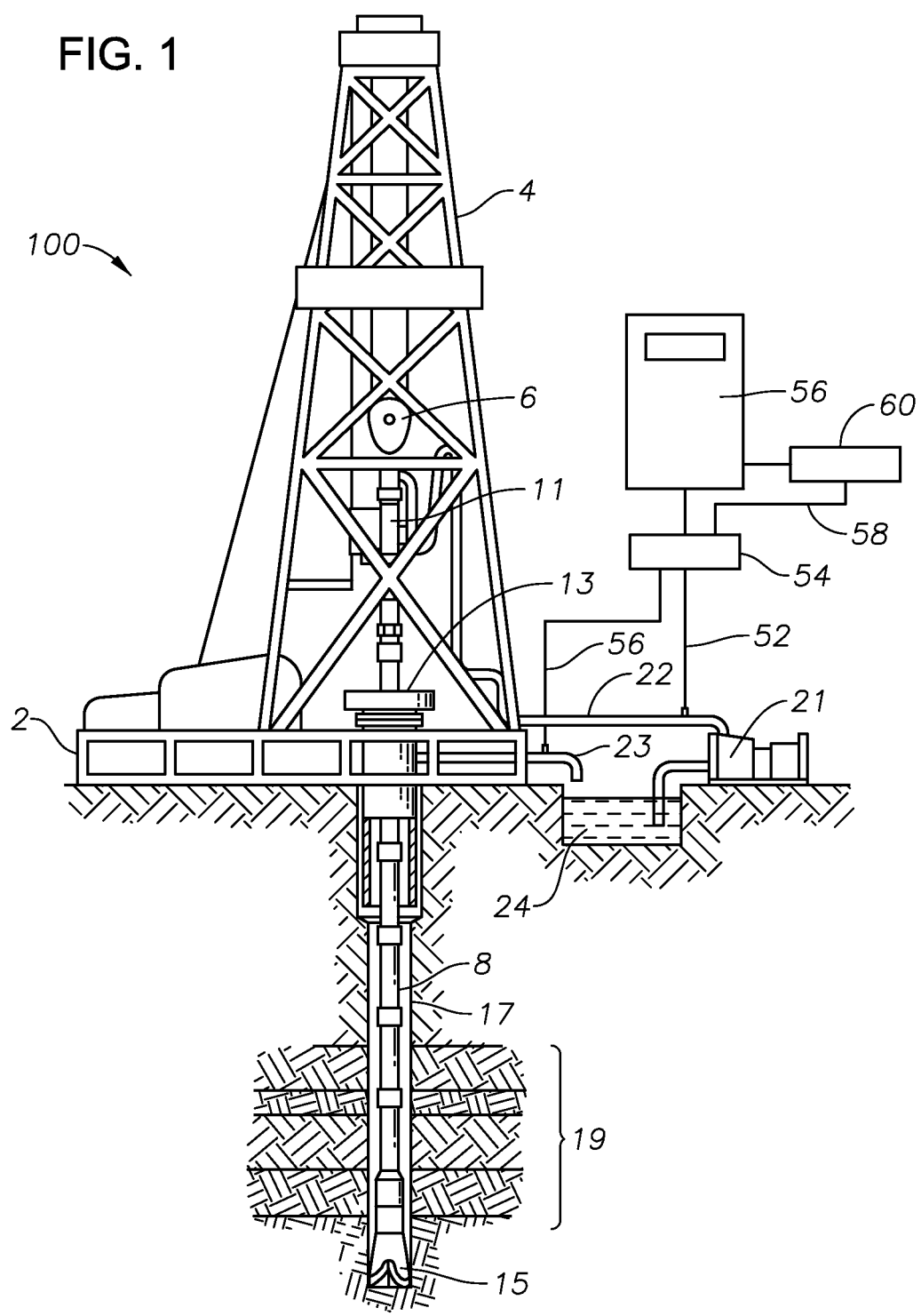
FIG. 1 illustrates a drilling rig system which may be utilized in conjunction with an illustrative embodiment of the present disclosure.

FIG. 1 illustrates a drilling rig system 100 which may be utilized in conjunction with an illustrative embodiment of the present disclosure. Referring back to FIG. 1, however, a drilling platform 2 is shown equipped with a derrick 4 that supports a hoist 6 for raising and lowering a drill string 8. Hoist 6 suspends a top drive 11 suitable for rotating drill string 8 and lowering it through well head 13. Connected to the lower end of drill string 8 is a drill bit 15. As drill bit 15 rotates, it creates a borehole 17 that passes through various formations 19. A drilling fluid circulation system includes a pump 21 for circulating drilling fluid through a supply pipe 22 to top drive 11, down through the interior of drill string 8, through orifices in drill bit 15, back to the surface via the annulus around drill string 8, and into a retention pit 24 via return pipe 23. The drilling fluid transports cuttings from the borehole into pit 24 and aids in maintaining the integrity of wellbore 16. Various materials can be used for drilling fluid, including, but not limited to, a salt-water based conductive mud.

An extractor 54 is fluidly coupled to the drilling circulation system via conduit 56 to extract an effluent gas sample from the drilling fluid exiting borehole 17 via return pipe 23. Extractor 54 is also fluidly coupled to supply pipe 22 via conduit 52 to thereby extract an influent gas sample from drilling fluid entering borehole 17. Extractor 54 may be any variety of such devices, as understood in the art. Although not shown, extractor 54 also includes a temperature detector for measuring the temperature of the effluent and influent gas samples, as well as a pressure detector to measure the pressure of the effluent and influent gas samples. An analytical instrument 60 is coupled to extractor 54, via line 58, which measured the effluent/influent gas samples to thereby determine an effluent vapor-phase molar contribution of each component of interest in the drilling fluid. Analytical instrument 60 may be a variety of devices, such as, for example, a gas chromatographer, a mass spectrometer or other gas analyzer. A computer processing unit ("CPU") 56 (also referred to herein as an information handling system) is coupled to extractor 54 and analytical instrument 60. CPU 56 comprises a processor and memory device containing a set of instructions that, when executed by the processor, causes the processor to determine a partial vapor pressure, a liquid-phase molar contribution and a vapor-phase molar contribution of each component of interest using a group contribution equilibrium model, as will be described in further detail below.

In alternative embodiments, separate extractors 54 may be utilized for the effluent and influent gas samples. For example, a first extractor may be fluidly coupled to return pipe 23 to extract an effluent gas sample from drilling fluid effluent exiting borehole 17. The first extractor may have a dedicated temperature detector (i.e., first temperature detector) coupled thereto to measure the temperature of the effluent gas sample. A first pressure detector could also be coupled thereto in order to measure the effluent pressure of the gas sample. A first analytical instrument (i.e., first gas analyzer) may be coupled to the first extractor to measure the effluent vapor-phase molar contribution of each component of interest in the drilling fluid effluent. At the same time, a second extractor could be coupled to supply pipe 22 to thereby extract an influent gas sample from drilling fluid influent entering borehole 17. The second extractor may also comprise a dedicated temperature detector (i.e., second temperature detector) and a dedicated pressure detector (i.e., second pressure detector) for measuring the influent temperature and pressure of the influent gas sample, respectively, in addition to being coupled to its own analytical instrument (i.e., second gas analyzer) to determine the vapor phase molar contributions. CPU 56 could therefore be operably connected to both extractors and their associated devices to thereby determine a partial vapor pressure, a liquid-phase molar contribution and a vapor-phase molar contribution of each component of interest using a group contribution equilibrium model, as will be described in further detail below.

It should also be noted that CPU 56 includes at least one processor and a non-transitory and computer-readable storage, all interconnected via a system bus. Software instructions executable by the processor for implementing the illustrative methods described herein in may be stored in local storage or some other computer-readable medium. It will also be recognized that the same software instructions may also be loaded into the storage from a CD-ROM or other appropriate storage media via wired or wireless methods.

Moreover, those ordinarily skilled in the art will appreciate that various aspects of the disclosure may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present disclosure. The disclosure may be practiced in distributed-computing environments where tasks are performed by remote-processing devices that are linked through a communications network. In a distributed-computing environment, program modules may be located in both local and remote computer-storage media including memory storage devices. The present disclosure may therefore, be implemented in connection with various hardware, software or a combination thereof in a computer system or other processing system.

Now that various illustrative embodiments of the present disclosure have been generally described, a more detail discussion of the method by which a group contribution equilibrium model is utilized to characterize drilling fluid components of interest will now be described. The intensive state of a thermodynamic system is established when its temperature, pressure, and the composition of all its phases are fixed. In equilibrium, these variables are not wholly independent, and the number of independent variables is given by the phase rule. For example, in a general vapor-liquid system, (with the temperature (T) and pressure (P) assumed to be uniform throughout) having m components, the independent variables are the temperature T, pressure P, m−1 liquid mole fractions, and m−1 vapor mole fractions. Of these 2m independent variables, the phase rule demonstrates that once m variables are known, the remaining m variables can determined by the simultaneous solution of m equilibrium equations:

$$f_i^L = f_i^V (i=1 \text{ to } j) \qquad \text{(Eq. 1)},$$

where $f_i^L$ and $f_i^V$ denote the fugacity of the liquid and vapor phases, respectively. In practice, parameters other than or in addition to fugacity may be used in the equation of state.

The use of a group contribution equilibrium equation of state method does not require additional laboratory testing to determine vapor-liquid equilibrium ("VLE"), liquid-liquid equilibrium ("LLE"), solid liquid equilibrium ("SLE"), and gas dissolved in liquid at pressures between 0 and 10 bar absolute and temperatures between 200 and 500 Kelvin. In certain illustrative embodiments of the present disclosure, the equations of state employ a group contribution model, such as, for example, Universal Quasi-Chemical Activity Coefficient ("UNIQUAC"), Universal Quasi-Chemical Functional-Group Activity Coefficient ("UNIFAC"), Modified UNIFAC, or Modified UNIFAC (Dortmund). As will be understood by those ordinarily skilled in the art having the benefit of this disclosure, a group contribution equilibrium model is a technique to estimate and predict thermodynamic and other properties from molecular structures based upon equilibrium. Knowing an approximate chemical composition of the liquid fluid phase and solid phase before contamination with geological formation materials, along with the detection of the gas phase and description of solid phase from the geological formation, allows for the determination of total detectable formation hydrocarbons at the surface and their concentration to be expressed as mole or mass fraction for materials coming from a well bore while drilling.

Figure 2:
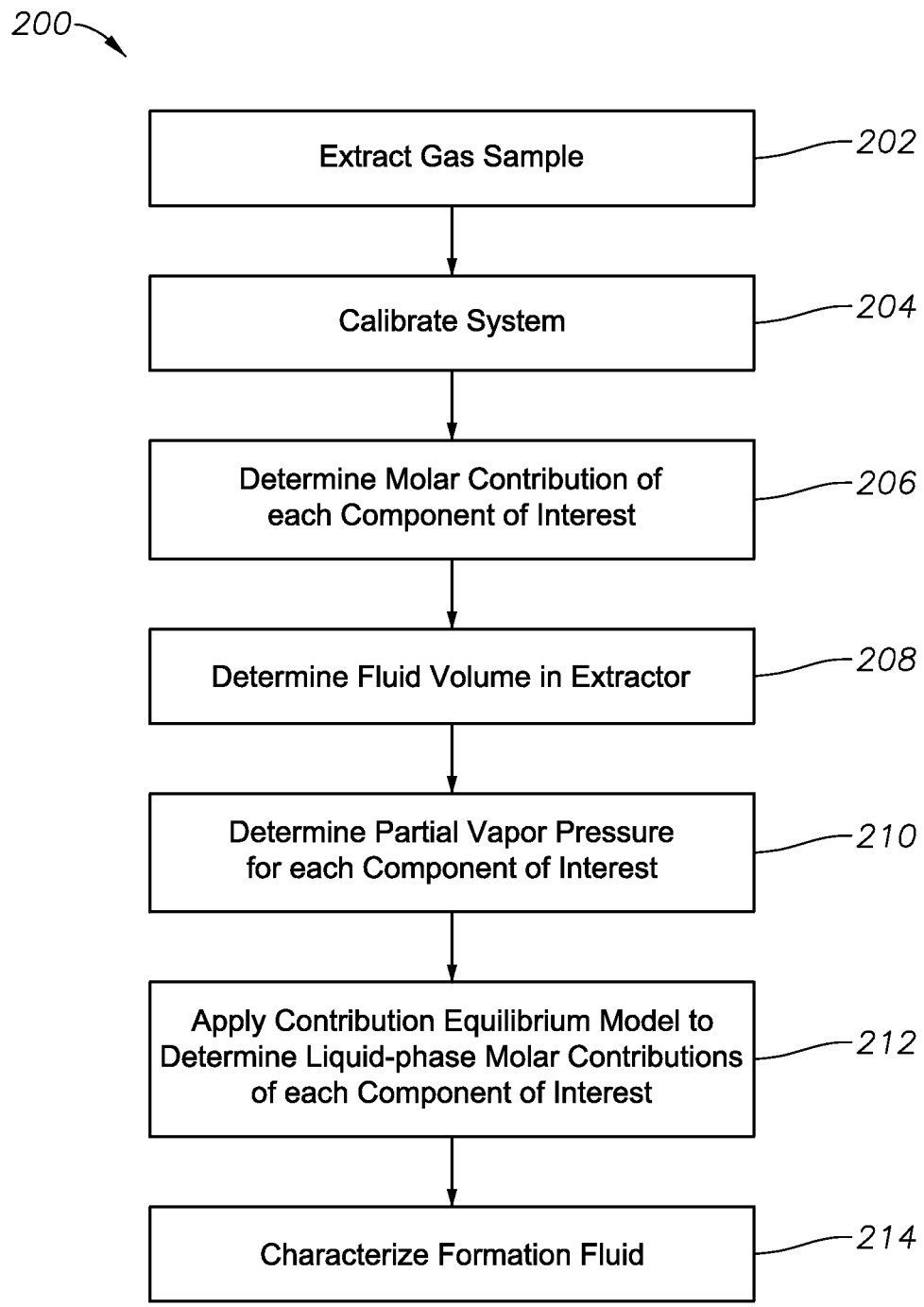
FIG. 2 is a flow chart of a method for characterizing formation fluid according to an illustrative method of the present disclosure.

FIG. 2 is a flow chart of a method 200 for characterizing formation fluid according to an illustrative method of the present disclosure. Such method will be performed by CPU 56 after extraction of one or more gas samples. Thus, with reference to FIGS. 1 and 2, at block 202, extractor 54 extracts a gas sample from a control volume of drilling fluid effluent that has been circulated through borehole 17. Note, however, that in alternative methods the extracted gas sample may be influent. In this method, the extraction occurs at a known pressure and temperature which is detected by the pressure/temperature detectors of extractor 54. Additionally, the volume of drilling fluid is known or can be estimated. Furthermore, in this embodiment, a carrier gas may be utilized to extract the gas sample.

At block 204, analytical instrument 60 is calibrated. Here, for example, a gas chromatographer may be utilized to calibrate mass spectrometer data. Alternatively, the mass spectrometer may be directly calibrated. Also, here analytical instrument 60 may convert the volume of the extracted gas sample from parts-per-million by volume (ppmv) to parts-per-million by mass (ppmm), if needed. At block 206, analytical instrument 60 determines the molar fraction/contribution of each components/species of interest from mass or volume concentration, as would be understood by those ordinarily skilled in the art having the benefit of this disclosure. Thereafter, based upon user input, CPU 56 removes the contribution of the carrier gas from the calculations, treats the carrier gas as an inert species in the system, or carries the carrier gas through subsequent calculations.

At block 208, CPU 56 determines the volume of fluid in extractor 54. Such a determination may be achieve using a variety of methods such as, for example, by estimating a cone's volume or a cone with the volume of a hemispherical topped cylinder removed, whichever is most accurate for a given system as determined based upon the geometry and flow rates of the system, as will be understood by those ordinarily skilled in the art having the benefit of this disclosure. At block 210, CPU 56 determines the partial vapor pressure ($P_{vpi}$) for each component of interest. Because all of the components typically of concern in the oil and gas industry are relatively light and well-known, may be determined using the Antoine vapor pressure equation:

$$\log_{10} P_{vpi} = A_i - \frac{B_i}{T + C_i}, \quad \text{(Eq. 2)}$$

where $A_i$, $B_i$, and $C_i$ are predetermined constants for species i and T is the temperature (° C.). Alternatively, techniques for estimating partial vapor pressure $P_{vpi}$ are available, as will be understood by those ordinarily skilled in the art having the benefit of this disclosure.

At block 212, CPU 56 utilizes a group contribution equilibrium model to determine the effluent liquid-phase molar contribution of each component of interest in the extracted gas sample. To achieve this in certain embodiments, CPU 56 solves a system of equations of state for group contribution equilibrium for the liquid-phase molar concentration ($x_i$) and the activity coefficient ($\gamma_i$) simultaneously as described in greater detail below. The activity coefficient $\gamma_i$ is ideally based on UNIQUAC, UNIFAC, modified UNIFAC, or Modified UNIFAC (Dortmund) equations. Using this data, CPU 56 then calculates the mass/moles of fluids and solids in extractor 54. All data of interest is then converted to moles using density and volume data (of the extracted gas) determined using a mass/density meter (which, in certain embodiments, forms part of extractor 54).

To solve for the state equations, CPU 56 may apply the following illustrative method. First, for most systems, Equation 1 above can be expressed as:

$$\gamma_i x_i \varphi_i^S P_{vpi}(PC)_i = \varphi_i y_i P (i=1 \text{ to } m) \quad \text{(Eq. 3)},$$

where $x_i$ is the liquid-phase molar concentration, $y_i$ is the vapor-phase molar concentration, $\gamma_i$ is the activity coefficient, $\varphi_i$ is the fugacity coefficient of the component in the mixture, $\varphi_i^S$ is the pure component fugacity coefficient at saturation of the component, $P_{vpi}$ is the partial vapor pressure, and $(PC)_i$ is the pressure correction factor for the ith component.

When pressure is at or below atmospheric pressure, the system can be assumed to be ideal, and the following relations apply:

$$\varphi_i = \varphi_i^S = (PC)_i = 1 \quad \text{(Eq. 4)}.$$

Accordingly, Equation 3 can be simplified as follows:

$$y_i P = x_i P_{vpi} \gamma_i \quad \text{(Eq. 5)}.$$

Equation 5 is rearranged to solve for the liquid-phase molar concentration $x_i$:

$$x_i = \frac{P y_i}{P_{vpi} \gamma_i}. \quad \text{(Eq. 6)}$$

The vapor-phase molar concentration $y_i$ is known for each component, as the value(s) has been measured by analytical instrument 60 (e.g., gas chromatographer, mass spectrometer, or other suitable instrument). Therefore, the partial vapor pressure $P_{vpi}$ is calculated by CPU 56 as described above.

The activity coefficient $\gamma_i$ is unknown, but may be determined using UNIQUAC, UNIFAC, modified UNIFAC, or Modified UNIFAC (Dortmund) equations, or another suitable model. In those embodiments applying the Modified UNIFAC (Dortmund) method, according to the model:

$$\ln \gamma_i = \ln \gamma_i^C + \ln \gamma_i^R \quad \text{(Eq. 7)},$$

where $\gamma_i$ is the activity coefficient of component i, $\gamma_i^C$ is the activity coefficient of component i combinational, and $\gamma_i^R$ is the activity coefficient of component i residual.

Furthermore, the following equations apply:

$$\ln \gamma_i^c = 1 - V_i' + \ln V_i' - 5 q_i \left(1 - \frac{V_i}{F_i} + \ln \frac{V_i}{F_i}\right), \quad \text{(Eq. 8)}$$

$$V_i' = \frac{r_i^{3/4}}{\sum_j x_j r_j^{3/4}}, \quad \text{(Eq. 9)}$$

$$V_i = \frac{r_i}{\sum_j x_j r_j}, \quad \text{(Eq. 10)}$$

$$F_i = \frac{q_i}{\sum_j x_j q_j}, \quad \text{(Eq. 11)}$$

where $x_i$ is the mole fraction of component i in the liquid phase, $V_i'$ is the modified volume/mole fraction of compound i in the mixture, $V_i$ is the volume/mole fraction of compound i in the mixture, $q_i$ is the relative van der Waals surface area of compound i, and $r_i$ is the relative van der Waals volume of compound i.

$$r_i = \sum_k v_k^{(i)} R_k, \quad \text{(Eq. 12)}$$

-continued $$q_i = \sum_k v_k^{(i)} Q_k, \qquad \text{(Eq. 13)}$$

where $R_k$ is the relative van der Waals volume of component k, $Q_k$ is the relative van der Waals surface area of the component, and $v_k^{(i)}$ is the number of structural groups of type k in molecule i.

$$\ln \gamma_i^R = \sum_k v_k^{(i)} (\ln \Gamma_k - \ln \Gamma_k^{(i)}), \qquad \text{(Eq. 14)}$$

$$\ln \Gamma_k = Q_k \left( 1 - \ln\left(\sum_m \Theta_m \Psi_{mk}\right) - \sum_m \frac{\Theta_m \Psi_{km}}{\sum_n \Theta_n \Psi_{nm}} \right), \qquad \text{(Eq. 15)}$$

where $\Gamma_k$ is the group activity coefficient of group k in the mixture, $\gamma_k^{(i)}$ is the group activity coefficient of group k in the pure substance i, $\Theta_m$ is the surface fraction of the group m in the liquid phase, and $\Psi_{nm}$ is the UNIFAQ temperature term.

$$\Theta_m = \frac{Q_m x_m}{\sum_n Q_n x_n}, \qquad \text{(Eq. 16)}$$

$$x_m = \frac{\sum_j v_m^{(j)} x_j}{\sum_j \sum_n v_n^{(j)} x_j}, \qquad \text{(Eq. 17)}$$

$$\Psi_{nm} = \exp\left(-\frac{a_{nm} + b_{nm} T + c_{nm} T^2}{T}\right) \approx \exp\left(-\frac{a_{nm}}{T}\right), \qquad \text{(Eq. 18)}$$

$$R_k = \frac{V_{wk}}{15.7}, \qquad \text{(Eq. 19)}$$

and $$Q_k = \frac{A_{wk}}{2.5 \times 10^9}, \qquad \text{(Eq. 20)}$$

where $x_m$ is the molar fraction of group m, T is absolute temperature (° K), $a_{nm}$, $b_{nm}$, and $c_{nm}$ are interaction parameters, $V_{wk}$ is van der Waals group volume of species k, and $A_{wk}$ is van der Waals group surface area of species k. In this illustrative method, Equations 6 through 20 above are solved simultaneously by CPU 56, thereby providing near-real-time liquid-phase molar concentration data.

At block 214, CPU 56 then determines at least one characteristic of the formation fluid. To achieve this in one illustrative method, from the moles of each component in the drilling effluent, the moles of the corresponding component of the drilling fluid are subtracted from influent entering the wellbore. The difference is the moles of each component attributable to the formation. In certain embodiments, the chemical composition of the drilling fluid may be determined from manufacturer data. Alternatively, the molar values of the components of interest of the drilling influent may be determined by extracting gas from a known control volume of drilling fluid influent to be circulated through the wellbore at a known pressure and temperature and repeating blocks 202-212 for the influent sample. By analyzing the drilling fluid influent in this manner, the contributions from gas carryover can be eliminated thereby providing more accurate data in subsequent analyses.

Thereafter, CPU 56 converts the data back to volume or mass fraction, ppmv, or ppmm based on the original detection units. The data is then corrected for equilibrium limitations. Using rate of penetration, bit and reamer size, and flow rate data, CPU 56 calculates the molar concentration of drilled formation and fluids per unit volume of drilling fluid. Specifically, the volume of drilled formation per foot drilled from bit and reamer size is the calculated, and the resulting data representing the fluid from formation by volume of formation drilled per lineal foot is normalized, which provides the characteristic of the formation fluid.

Figure 3:
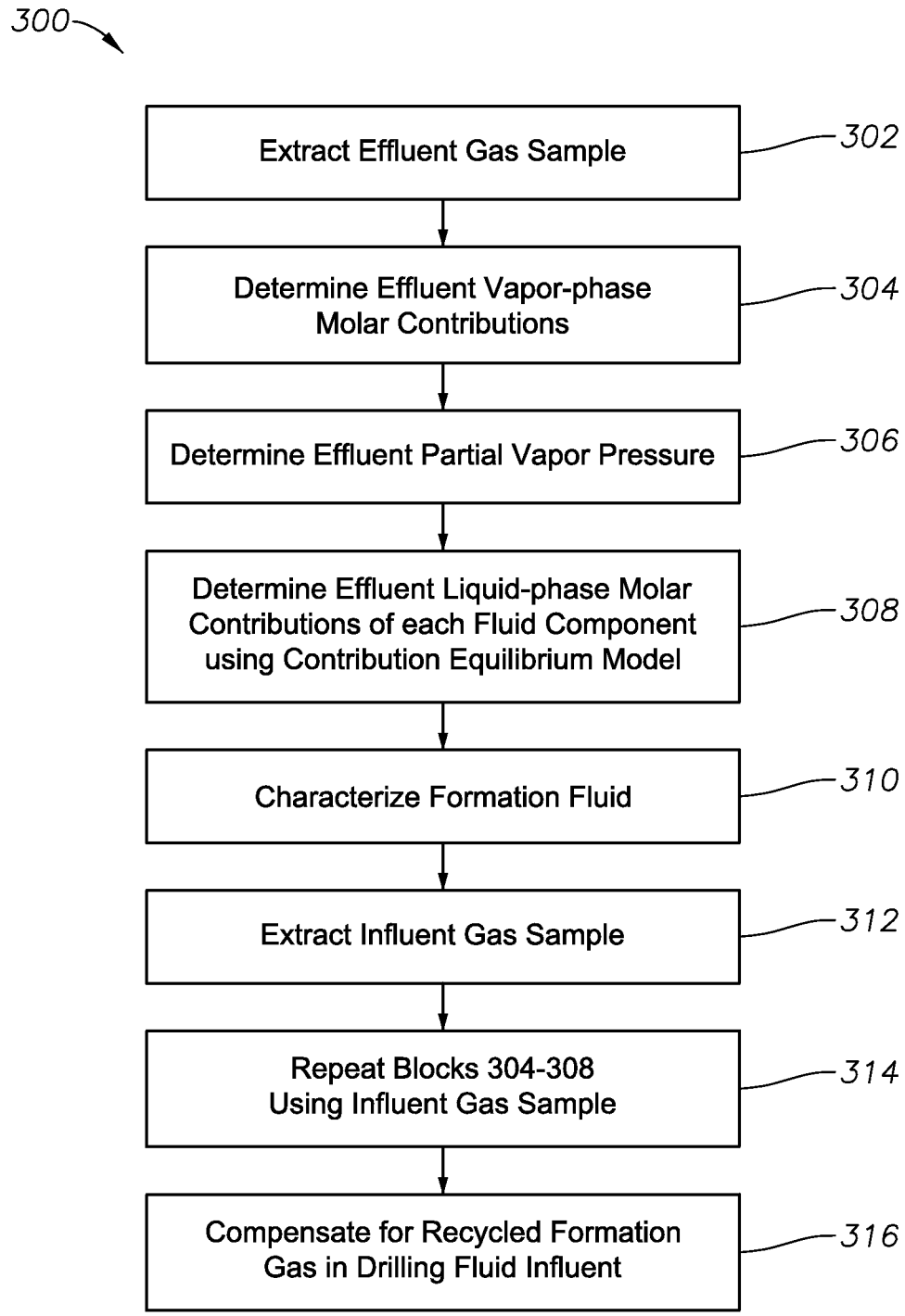
FIG. 3 is a flow chart illustrative another method 300 to characterize formation fluid in which the effluent and influent samples are utilized, according to an illustrative method of the present disclosure.

FIG. 3 is a flow chart illustrative another method 300 to characterize formation fluid in which the effluent and influent samples are utilized, according to an illustrative method of the present disclosure. Like the method described above, certain steps of method 300 may be performed wholly or partially within CPU 56. At block 302, an effluent gas sample is extracted from exit pipe 23 via conduit 56 via a drilling operation. The temperature and pressure of the sample may be simultaneously measured using the temperature and pressure sensors described above. At block 304, the effluent vapor-phase molar contribution of each component of interest in the drilling fluid is determined. For example, the vapor-phase molar contribution of each component of interest in the effluent gas sample may be measured by analytical instrument 60 (e.g., gas chromatograph, mass spectrometer, or other suitable instrument).

At block 306, CPU 56 determines the effluent partial vapor pressure using the effluent temperature measurement received from the temperature detectors of extractor 54 and one or more of the equations described above with reference to FIG. 2. At block 308, CPU 56 then calculates the effluent liquid-phase molar contribution of each component using the determined effluent partial vapor pressure and the determined effluent vapor-phase molar contribution according to a vapor-liquid group contribution equilibrium equation of state, as previously described. Here, a first and second group contribution equilibrium equation of state would be utilized for the effluent and influent fluids, respectively. At block 310, CPU 56 then determines at least one characteristic of the formation fluid by subtracting the known composition of the influent drilling fluid from the sum of the effluent vapor-phase and liquid-phase molar contributions of all the components. As previously described in one illustrative method, the chemical composition of the drilling fluid may be determined from manufacturer data.

At block 312, an influent gas sample is then extracted from supply pipe 22 via conduit 52. At block 314, blocks 304-308 above are then repeated for the influent sample. As such, the influent gas sample is measured to determine an influent vapor-phase molar contribution of each component in the drilling fluid influent. The influent partial vapor pressure for each component is then determined using the influent temperature. The influent liquid-phase molar contribution of each component is the determined using the influent partial vapor pressure and influent vapor-phase molar contributions using the vapor-liquid group contribution equilibrium equations of state, as previously described. Thereafter, at block 316, though use of the influent vapor-phase and liquid-phase molar contributions and a known composition of virgin drilling fluid, CPU 56 may then compensate for any recycled formation gas in the drilling fluid influent. Accordingly, the integrity of subsequent fluid characterizations will be maintained.

Accordingly, the illustrative methods and embodiments described herein provide real-time characterization of drilling fluid. The system described herein may be installed at a drilling site and practiced in real time during drilling operations without the need to obtain experimental correction factors. Hence, a drilling operation may be initiated and the formation fluids accurately characterized in real time at the drilling site, thus allowing drilling operations to be altered in real-time based on the characterized formation fluid data.

Embodiments described herein further relate to any one or more of the following paragraphs:

1. A method for characterizing formation fluid, comprising extracting a gas sample from a fluid exposed to a formation during downhole operations; measuring a temperature of the gas sample; determining from the gas sample a vapor-phase molar contribution of each of one or more components of interest in the fluid; determining a partial vapor pressure for each component of interest using the temperature; determining a liquid-phase molar contribution of each component of interest using the determined partial vapor pressure and the determined vapor-phase molar contribution and a vapor-liquid group contribution equilibrium equation of state; and subtracting a known chemical composition of the drilling fluid from a sum of the determined vapor-phase and liquid-phase molar contributions of all components to characterize the formation fluid.

2. The method of paragraph 1, wherein extracting the gas sample comprises extracting an effluent or influent gas sample.

3. The method of paragraphs 1 or 2, wherein calculating the liquid-phase molar contribution of each component further comprises for each of the one or more components, equating a liquid-phase fugacity to a vapor-phase fugacity, in which the vapor-phase fugacity is a mathematical product of the vapor-phase molar contribution, a vapor-phase fugacity coefficient of the component in the fluid, and the pressure; and in which the liquid-phase fugacity is a mathematical product of at least the liquid-phase molar contribution, a liquid-phase fugacity coefficient of the component as a pure substance at saturation, and an activity coefficient of the component; and for all of the one or more components collectively, simultaneously solving a system of group contribution equations of state for the liquid-phase molar contribution(s) and the activity coefficient(s).

4. The method of any of paragraphs 1-3, wherein the activity coefficient(s) are based on equations from one of the group comprising a Universal Quasi-Chemical Activity Coefficient Model, a Universal Quasi-Chemical Functional-Group Activity Coefficient Model, a modified Universal Quasi-Chemical Functional-Group Activity Coefficient Model, and a Dortmund modified Universal Quasi-Chemical Functional-Group Activity Coefficient Model.

5. The method of any of paragraphs 1-4, wherein determining the partial vapor pressure for each the component further comprises calculating the partial vapor pressure for each the component using an Antoine vapor pressure equation.

6. The method of any of paragraphs 1-5, further comprising extracting an influent gas sample at a influent temperature and a influent pressure from a fluid influent entering a borehole in the formation during downhole operations; measuring the influent gas sample to determine an influent vapor-phase molar contribution of each of the components in the fluid influent; determining an influent partial vapor pressure for each the component using the influent temperature; and determining an influent liquid-phase molar contribution of each component using the influent partial vapor pressure and the influent vapor-phase molar contribution and the vapor-liquid group contribution equilibrium equation of state, whereby the influent vapor-phase and influent liquid-phase molar contributions of all the components and a known chemical composition of virgin fluid collectively define a composition of influent fluid, thereby compensating for recycled formation gas in the fluid influent.

7. The method of any of paragraphs 1-6, further comprising extracting a volume of the gas sample using a carrier gas; using at least one of the group comprising a gas chromatographer or a mass spectrometer to measure the vapor-phase molar contribution of each the component; removing a carrier gas contribution from the vapor-phase molar concentration(s); and normalizing the formation fluid by a volume of formation drilled per lineal depth.

8. A system for characterizing formation fluid, comprising a gas extractor fluidly coupled to a flow of fluid within a downhole fluid circulation system; a temperature detector coupled to the extractor; a pressure detector coupled to the extractor; gas analyzer that selectively generates an output corresponding to a vapor-phase molar contribution of each of one or more components of interest in the fluid when exposed to a gas sample of the fluid obtained by the gas extractor; and an information handling system coupled to the temperature detector, the pressure detector, and the gas analyzer, the information handling system comprising a processor and memory device containing a set of instructions that, when executed by the processor, causes the processor to: determine an partial vapor pressure for each the component using the temperature of the gas sample; calculate a liquid-phase molar contribution of each the component of interest using the partial vapor pressure and the vapor-phase molar contribution according to a vapor-liquid equilibrium group contribution equation of state; and subtract a known chemical composition of the fluid from a sum of the determined vapor-phase and liquid-phase molar contributions of all components to characterize the formation fluid.

9. The system of paragraph 8, wherein the gas sample is an effluent or influent gas sample.

10. The system of paragraphs 8 or 9, wherein the set of instructions further cause the processor to: for each of the one or more components, equate a liquid-phase fugacity to a vapor-phase fugacity, in which the vapor-phase fugacity is a mathematical product of the vapor-phase molar contribution, a vapor-phase fugacity coefficient of the component in the fluid, and the pressure, and in which the liquid-phase fugacity is a mathematical product of at least the effluent liquid-phase molar contribution, a liquid-phase fugacity coefficient of the component as a pure substance at saturation, and an activity coefficient of the component; and for all of the one or more components collectively, simultaneously solve a system of equations of state for the liquid-phase molar contribution(s) and the activity coefficient(s).

11. The system of any of paragraphs 8-10, wherein the activity coefficient(s) are based on equations from one of the group comprising a Universal Quasi-Chemical Activity Coefficient Model, a Universal Quasi-Chemical Functional-Group Activity Coefficient Model, a modified Universal Quasi-Chemical Functional-Group Activity Coefficient Model, and a Dortmund modified Universal Quasi-Chemical Functional-Group Activity Coefficient Model.

12. The system of any of paragraphs 8-11, wherein the set of instructions further cause the processor to calculate the partial vapor pressure for each the component using an Antoine vapor pressure equation.

13. The system of any of paragraphs 8-12, wherein the gas analyzer includes at least one from the group comprising a gas chromatographer and a mass spectrometer.

14. A system for characterizing formation fluid, comprising a first extractor fluidly coupled to a fluid circulation system of a borehole in the earth, the first extractor arranged for extracting an effluent gas sample from a fluid effluent exiting the borehole; a first temperature detector coupled to the first extractor for measuring an effluent temperature of the effluent gas sample; a first pressure detector coupled to the first extractor for measuring an effluent pressure of the effluent gas sample; a first gas analyzer coupled to the first extractor and arranged to selectively generate an output corresponding to an effluent vapor-phase molar contribution of each of one or more components of interest in the fluid effluent when exposed to a gas sample of the fluid effluent obtained by the gas extractor; a second extractor fluidly coupled to the fluid circulation system arranged for extracting an influent gas sample from a fluid influent entering the borehole; a second temperature detector coupled to the second extractor for measuring an influent temperature of the influent gas sample; a second pressure detector coupled to the second extractor for measuring an influent pressure of the influent gas sample; a second gas analyzer coupled to the second extractor and arranged to selectively generate an output corresponding to an influent vapor-phase molar contribution of each of one or more components of interest in the fluid influent when exposed to a gas sample of the drilling fluid influent obtained by the gas extractor; and an information handling system coupled to the first and second temperature detectors, the first and second pressure detector, and the first and second gas analyzers, the information handling system comprising a processor and memory device containing a set of instructions that, when executed by the processor, causes the processor to: determine an influent partial vapor pressure for each the component using the influent temperature of the influent gas sample; determine an influent liquid-phase molar contribution of each the component using the influent partial vapor pressure and the influent vapor-phase molar contribution according to a vapor-liquid equilibrium group contribution equation of state; determine an effluent partial vapor pressure for each the component using the effluent temperature of the effluent gas sample; determine an effluent liquid-phase molar contribution of each the component using the effluent partial vapor pressure and the effluent vapor-phase molar contribution according to a vapor-liquid equilibrium group contribution equation of state; and subtract the determined influent vapor-phase and liquid-phase molar contributions of all the components and a known chemical composition of fluid from a sum of the determined effluent vapor-phase and liquid-phase molar contributions of all the components to characterize the formation fluid.

15. The system of paragraphs 14, wherein the set of instructions further cause the processor to: for each of the one or more components, equate an effluent liquid-phase fugacity to an effluent vapor-phase fugacity, in which the effluent vapor-phase fugacity is a mathematical product of the effluent vapor-phase molar contribution, a vapor-phase fugacity coefficient of the component in the fluid effluent, and the pressure, and in which the effluent liquid-phase fugacity is a mathematical product of at least the effluent liquid-phase molar contribution, a liquid-phase fugacity coefficient of the component as a pure substance at saturation, and an activity coefficient of the component; and for all of the one or more components collectively, simultaneously solve a first system of group contribution equations of state for the effluent liquid-phase molar contribution(s) and the activity coefficient(s).

16. The system of paragraphs 14 or 15, wherein the set of instructions further cause the processor to: for each of the one or more components, equate an influent liquid-phase fugacity to an influent vapor-phase fugacity, in which the influent vapor-phase fugacity is a mathematical product of the influent vapor-phase molar contribution, a vapor-phase fugacity coefficient of the component in the fluid influent, and the pressure, and in which the influent liquid-phase fugacity is a mathematical product of the influent liquid-phase molar contribution, the liquid-phase fugacity coefficient of the component as a pure substance at saturation, and the activity coefficient of the component; and for all of the one or more components collectively, simultaneously solve a second system of group contribution equations of state for the influent liquid-phase molar contribution(s) and the activity coefficient(s).

17. The system of any of paragraphs 14-16, wherein the activity coefficient(s) are based on equations from one of the group consisting of a Universal Quasi-Chemical Activity Coefficient Model, a Universal Quasi-Chemical Functional-Group Activity Coefficient Model, a modified Universal Quasi-Chemical Functional-Group Activity Coefficient Model, and a Dortmund modified Universal Quasi-Chemical Functional-Group Activity Coefficient Model.

18. The system of any of paragraphs 14-17, wherein the set of instructions further cause the processor to calculate the effluent partial vapor pressure for each the component using an Antoine vapor pressure equation; and calculate the influent partial vapor pressure for each the component using the Antoine vapor pressure equation.

19. A method for characterizing formation fluid, comprising extracting an effluent gas sample from fluid of a borehole; determining an effluent liquid-phase molar contribution of each component of the effluent gas sample using a vapor-liquid group contribution equilibrium equation of state; and characterizing formation fluid based upon the effluent liquid-phase molar contribution of each component of the effluent gas sample.

20. The method of paragraph 19, further comprising extracting an influent gas sample from the fluid of the borehole; determining an influent liquid-phase molar contribution of each component of the influent gas sample using a second vapor-liquid group contribution equilibrium equation of state; and compensating for recycled formation gas in the fluid through analysis of the influent liquid-phase molar contributions of all the components and a known chemical composition of virgin fluid.

Moreover, any of the methods described herein may be embodied within a system comprising processing circuitry to implement any of the methods, or a in a computer-program product comprising instructions which, when executed by at least one processor, causes the processor to perform any of the methods described herein.

Although various embodiments and methods have been shown and described, the disclosure is not limited to such embodiments and methods and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A method for characterizing formation fluid, comprising:
    extracting a gas sample from a fluid exposed to a formation during downhole operations;
    predetermining a chemical composition of a virgin fluid prior to exposing the virgin fluid to the formation;
    exposing the virgin fluid to the formation;
    measuring a temperature of the gas sample;
    determining from the gas sample a vapor-phase molar contribution of each of one or more components of interest in the fluid exposed to the formation;
    determining a partial vapor pressure for each component of interest using the temperature;
    determining a liquid-phase molar contribution of each component of interest using the determined partial vapor pressure and the determined vapor-phase molar contribution and a vapor-liquid group contribution equilibrium equation of state; and
    subtracting the predetermined chemical composition of the virgin fluid from a sum of the determined vapor-phase and liquid-phase molar contributions of all the components of the fluid exposed to the formation to characterize the formation fluid.

2. The method of claim 1, wherein extracting the gas sample comprises extracting an effluent or influent gas sample.

3. The method of claim 1, wherein calculating the liquid-phase molar contribution of each component further comprises:
    for each of the one or more components, equating a liquid-phase fugacity to a vapor-phase fugacity, in which the vapor-phase fugacity is a mathematical product of the vapor-phase molar contribution, a vapor-phase fugacity coefficient of the component in the fluid, and the pressure, and in which the liquid-phase fugacity is a mathematical product of at least the liquid-phase molar contribution, a liquid-phase fugacity coefficient of the component as a pure substance at saturation, and an activity coefficient of the component; and
    for all of the one or more components collectively, simultaneously solving a system of group contribution equations of state for the liquid-phase molar contribution(s) and the activity coefficient(s).

4. The method of claim 3, wherein the activity coefficient(s) are based on equations from one of the group comprising a Universal Quasi-Chemical Activity Coefficient Model, a Universal Quasi-Chemical Functional-Group Activity Coefficient Model, a modified Universal Quasi-Chemical Functional-Group Activity Coefficient Model, and a Dortmund modified Universal Quasi-Chemical Functional-Group Activity Coefficient Model.

5. The method of claim 1, wherein determining the partial vapor pressure for each the component further comprises calculating the partial vapor pressure for each the component using an Antoine vapor pressure equation.

6. The method of claim 1, further comprising:
    extracting an influent gas sample at a influent temperature and a influent pressure from a fluid influent entering a borehole in the formation during downhole operations;
    measuring the influent gas sample to determine an influent vapor-phase molar contribution of each of the components in the fluid influent;
    determining an influent partial vapor pressure for each the component using the influent temperature; and
    determining an influent liquid-phase molar contribution of each component using the influent partial vapor pressure and the influent vapor-phase molar contribution and the vapor-liquid group contribution equilibrium equation of state,
    whereby the influent vapor-phase and influent liquid-phase molar contributions of all the components and a known chemical composition of virgin fluid collectively define a composition of influent fluid, thereby compensating for recycled formation gas in the fluid influent.

7. The method of claim 1, further comprising:
    extracting a volume of the gas sample using a carrier gas;
    using at least one of the group comprising a gas chromatographer or a mass spectrometer to measure the vapor-phase molar contribution of each the component;
    removing a carrier gas contribution from the vapor-phase molar concentration(s); and
    normalizing the formation fluid by a volume of formation drilled per lineal depth.

8. A system for characterizing formation fluid, comprising:
    a virgin fluid that circulates in a downhole fluid circulation system;
    a gas extractor fluidly coupled to a flow of fluid within a downhole fluid circulation system;
    a temperature detector coupled to the extractor;
    a pressure detector coupled to the extractor;
    gas analyzer that selectively generates an output corresponding to a vapor-phase molar contribution of each of one or more components of interest in the flow of fluid when exposed to a gas sample of the flow of fluid obtained by the gas extractor; and
    an information handling system coupled to the temperature detector, the pressure detector, and the gas analyzer, the information handling system comprising a processor and memory device containing a set of instructions that, when executed by the processor, causes the processor to:
        determine a partial vapor pressure for each the component using the temperature of the gas sample;
        calculate a liquid-phase molar contribution of each the component of interest using the partial vapor pressure and the vapor-phase molar contribution according to a vapor-liquid equilibrium group contribution equation of state; and
    subtract a chemical composition of the virgin fluid from a sum of the determined vapor-phase and liquid-phase molar contributions of all the components in the flow of fluid to characterize the formation fluid.

9. The system of claim 8, wherein the gas sample is an effluent or influent gas sample.

10. The system of claim 8, wherein the set of instructions further cause the processor to:
    for each of the one or more components, equate a liquid-phase fugacity to a vapor-phase fugacity, in which the vapor-phase fugacity is a mathematical product of the vapor-phase molar contribution, a vapor-phase fugacity coefficient of the component in the fluid, and the pressure, and in which the liquid-phase fugacity is a mathematical product of at least the effluent liquid-phase molar contribution, a liquid-phase fugacity coefficient of the component as a pure substance at saturation, and an activity coefficient of the component; and for all of the one or more components collectively, simultaneously solve a system of equations of state for the liquid-phase molar contribution(s) and the activity coefficient(s).

11. The system of claim 10, wherein the activity coefficient(s) are based on equations from one of the group comprising a Universal Quasi-Chemical Activity Coefficient Model, a Universal Quasi-Chemical Functional-Group Activity Coefficient Model, a modified Universal Quasi-Chemical Functional-Group Activity Coefficient Model, and a Dortmund modified Universal Quasi-Chemical Functional-Group Activity Coefficient Model.

12. The system of claim 8, wherein the set of instructions further cause the processor to calculate the partial vapor pressure for each the component using an Antoine vapor pressure equation.

13. The system of claim 8, wherein the gas analyzer includes at least one from the group comprising a gas chromatograph and a mass spectrometer.

14. A system for characterizing formation fluid, comprising:
　a first extractor fluidly coupled to a fluid circulation system of a borehole in the earth, the first extractor arranged for extracting an effluent gas sample from a fluid effluent exiting the borehole;
　a first temperature detector coupled to the first extractor for measuring an effluent temperature of the effluent gas sample;
　a first pressure detector coupled to the first extractor for measuring an effluent pressure of the effluent gas sample;
　a first gas analyzer coupled to the first extractor and arranged to selectively generate an output corresponding to an effluent vapor-phase molar contribution of each of one or more components of interest in the fluid effluent when exposed to a gas sample of the fluid effluent obtained by the gas extractor;
　a second extractor fluidly coupled to the fluid circulation system arranged for extracting an influent gas sample from a fluid influent entering the borehole;
　a second temperature detector coupled to the second extractor for measuring an influent temperature of the influent gas sample;
　a second pressure detector coupled to the second extractor for measuring an influent pressure of the influent gas sample;
　a second gas analyzer coupled to the second extractor and arranged to selectively generate an output corresponding to an influent vapor-phase molar contribution of each of one or more components of interest in the fluid influent when exposed to a gas sample of the drilling fluid influent obtained by the gas extractor; and
　an information handling system coupled to the first and second temperature detectors, the first and second pressure detector, and the first and second gas analyzers, the information handling system comprising a processor and memory device containing a set of instructions that, when executed by the processor, causes the processor to:
　　determine an influent partial vapor pressure for each the component using the influent temperature of the influent gas sample;
　　determine an influent liquid-phase molar contribution of each the component using the influent partial vapor pressure and the influent vapor-phase molar contribution according to a vapor-liquid equilibrium group contribution equation of state;
　　determine an effluent partial vapor pressure for each the component using the effluent temperature of the effluent gas sample;
　　determine an effluent liquid-phase molar contribution of each the component using the effluent partial vapor pressure and the effluent vapor-phase molar contribution according to a vapor-liquid equilibrium group contribution equation of state; and
　　subtract the determined influent vapor-phase and liquid-phase molar contributions of all the components of the fluid influent from a sum of the determined effluent vapor-phase and liquid-phase molar contributions of all the components of the fluid effluent to characterize the formation fluid.

15. The system of claim 14, wherein the set of instructions further cause the processor to:
　for each of the one or more components, equate an effluent liquid-phase fugacity to an effluent vapor-phase fugacity, in which the effluent vapor-phase fugacity is a mathematical product of the effluent vapor-phase molar contribution, a vapor-phase fugacity coefficient of the component in the fluid effluent, and the pressure, and in which the effluent liquid-phase fugacity is a mathematical product of at least the effluent liquid-phase molar contribution, a liquid-phase fugacity coefficient of the component as a pure substance at saturation, and an activity coefficient of the component; and
　for all of the one or more components collectively, simultaneously solve a first system of group contribution equations of state for the effluent liquid-phase molar contribution(s) and the activity coefficient(s).

16. The system of claim 15, wherein the set of instructions further cause the processor to:
　for each of the one or more components, equate an influent liquid-phase fugacity to an influent vapor-phase fugacity, in which the influent vapor-phase fugacity is a mathematical product of the influent vapor-phase molar contribution, a vapor-phase fugacity coefficient of the component in the fluid influent, and the pressure, and in which the influent liquid-phase fugacity is a mathematical product of the influent liquid-phase molar contribution, the liquid-phase fugacity coefficient of the component as a pure substance at saturation, and the activity coefficient of the component; and
　for all of the one or more components collectively, simultaneously solve a second system of group contribution equations of state for the influent liquid-phase molar contribution(s) and the activity coefficient(s).

17. The system of claim 16, wherein the activity coefficient(s) are based on equations from one of the group consisting of a Universal Quasi-Chemical Activity Coefficient Model, a Universal Quasi-Chemical Functional-Group Activity Coefficient Model, a modified Universal Quasi-Chemical Functional-Group Activity Coefficient Model, and a Dortmund modified Universal Quasi-Chemical Functional-Group Activity Coefficient Model.

18. The system of claim 14, wherein the set of instructions further cause the processor to:
　calculate the effluent partial vapor pressure for each the component using an Antoine vapor pressure equation; and
　calculate the influent partial vapor pressure for each the component using the Antoine vapor pressure equation.

19. A method for characterizing formation fluid, comprising:
　predetermining a chemical composition of a virgin fluid;
　extracting an effluent gas sample from fluid of a borehole;

determining an effluent liquid-phase molar contribution of each component of the effluent gas sample using a vapor-liquid group contribution equilibrium equation of state; and characterizing formation fluid based upon the effluent liquid-phase molar contribution of each component of the effluent gas sample by subtracting the chemical composition of the virgin fluid from a sum of the determined effluent vapor-phase and liquid-phase molar contributions of all the components of the fluid of the borehole.

20. The method of claim 19, further comprising:

extracting an influent gas sample from the fluid of the borehole;

determining an influent liquid-phase molar contribution of each component of the influent gas sample using a second vapor-liquid group contribution equilibrium equation of state; and compensating for recycled formation gas in the fluid through analysis of the influent liquid-phase molar contributions of all the components and a known chemical composition of virgin fluid.

* * * * *